(12) United States Patent
Parent et al.

(10) Patent No.: US 7,858,705 B2
(45) Date of Patent: Dec. 28, 2010

(54) FUNCTIONALISED POLYOLEFINS, MOISTURE CURABLE POLYOLEFIN RESINS AND PROCESSES OF MANUFACTURER THEREOF

(75) Inventors: John Scott Parent, Kingston (CA); Saurav Sankar Sengupta, Kingston (CA)

(73) Assignee: Queen's University At Kingston, Kingston, Ontario (CA)

( * ) Notice: Subject to any disclaimer, the term of this patent is extended or adjusted under 35 U.S.C. 154(b) by 746 days.

(21) Appl. No.: 11/266,487

(22) Filed: Nov. 4, 2005

(65) Prior Publication Data

US 2006/0116480 A1 Jun. 1, 2006

Related U.S. Application Data

(60) Provisional application No. 60/625,594, filed on Nov. 8, 2004.

(51) Int. Cl.
*C08F 297/02* (2006.01)
*C08F 297/00* (2006.01)

(52) U.S. Cl. ............ 525/240; 525/303; 525/322; 525/342; 525/455

(58) Field of Classification Search ........... 525/240, 525/326.3, 326.5, 332.5, 342, 303, 322, 455
See application file for complete search history.

(56) References Cited

U.S. PATENT DOCUMENTS

| | | | | |
|---|---|---|---|---|
| 3,965,054 | A * | 6/1976 | Nojiri et al. | 521/96 |
| 3,996,310 | A * | 12/1976 | Floyd et al. | 525/136 |
| 4,032,592 | A * | 6/1977 | Ogihara et al. | 525/263 |
| 4,058,583 | A | 11/1977 | Glander et al. | 264/176 R |
| 4,256,558 | A | 3/1981 | Inata et al. | |
| 4,540,527 | A | 9/1985 | Field et al. | |
| 5,071,928 | A | 12/1991 | Ciardelli et al. | |
| 5,227,442 | A | 7/1993 | Babu et al. | |
| 5,376,716 | A * | 12/1994 | Nayak et al. | 524/295 |
| 5,382,633 | A | 1/1995 | Scott et al. | |
| 5,719,251 | A | 2/1998 | Wilczek et al. | |
| 5,898,054 | A * | 4/1999 | Saito et al. | 526/206 |
| 6,184,316 | B1 | 2/2001 | Masi et al. | |
| 6,451,919 | B1 | 9/2002 | Aglietto et al. | |
| 6,844,412 | B2 * | 1/2005 | Halladay | 528/25 |
| 7,217,486 | B2 * | 5/2007 | Kato et al. | 430/108.6 |
| 2005/0108832 | A1 | 5/2005 | Torri et al. | |

FOREIGN PATENT DOCUMENTS

| | | |
|---|---|---|
| EP | 0073435 A2 | 3/1983 |
| EP | 0268486 B1 | 5/1988 |
| EP | 0 073 435 B1 | 9/1989 |
| EP | 0342792 B1 | 10/1993 |

| | | |
|---|---|---|
| WO | WO 2004/113399 A2 | 12/2004 |

OTHER PUBLICATIONS

Al-Malaika, S., et al., "Reactive procesing of polymers: mechanisms of grafting reactions of functional antioxidants on polyolefins in the presence of a coagent." *Polymer Degradation and Stability* 409: 77-89 (1995).

Coiai, S., et al., "Control of degradation reactions during radical functionalization of polypropylene in the melt." *Macromolecules* 37: 8414-8423 (2004).

Mulhaupt, R., et al., "Functional Polypropylene blend compatibilizers." *Makromol. Chem., Macromol. Symp.* 48/49: 317-332 (1991).

Ohno, A., et al., "Thermal and Photolytic Decompositions of azobis(2-phenylthio)-2-propane." *Bulletin of the Chemical Society of Japan* 44: 463-467 (1971).

Parent, J.S., et al., "Terminal functionalization of polypropylene by radical-mediated thiol-ene addition." *Macromolecules* 38: 5538-5544 (2005).

(Continued)

*Primary Examiner*—Irina S Zemel
(74) *Attorney, Agent, or Firm*—Omar A. Nassif (57) ABSTRACT

A process for preparing a functionalised polyolefin is described. The process comprises the step of reacting: (i) a polyolefin, (ii) a compound containing a functional group, and (iii) a coagent compound having Formula I:

$$X_n\text{—}Y\text{—}Z_m \qquad (I)$$

wherein:
Y is a core moiety;
Z is a moiety containing a carbon-carbon double bond or a carbon-carbon triple bond;
X is a moiety different than Z and the bond between X and Y may be a single bond or a double bond;
n is a whole number greater than or equal to 0;
m is a whole number greater than or equal to 2; and
m+n equals a number up to the valence of Y;

wherein: (a) when m is 2 and n is 0, the process comprises initially reacting the polyolefin and the coagent to form a product that is then reacted with the compound containing the functional group, and (b) the compound containing a functional group is substantially inert in free radical-mediated polymerization reactions and in free radical-mediated grafting reactions. The invention also relates to a functionalized polyolefin produced by such a process. The polyolefins, particularly high molecular weight polyolefins (Mn>10,000), can be extensively modified with functional groups (e.g., thiols, epoxides, anhydrides, carboxylic acids, amines, amides, boron-containing compounds, silicon-containing compounds, cyano-containing compounds, sulfates, sulfonates, sulfites, esters, thioesters, dithioesters, ether, halides, phosphates, phosphonates, phosphines, phosphites and other compounds containing polar moieties) without altering molecular weight thereby rendering the functionalised polyolefins useful in a wide range of applications.

50 Claims, 1 Drawing Sheet

OTHER PUBLICATIONS

Sengupta, S.S., et al., "Radical-mediated modification of polypropylene: selective grafting via polyallyl coagents." *Journal of Polymer Science* 43: 4882-4893 (2005).

Zhang, L.-F., et al., "Studies on the technique and mechanism of solid grafting of polypropylene with dual monomers." *Chemical Journal of Chinese Universities* 22: 1406-1409 (2001)(translation).

Moad, G., "The synthesis of polyolefin graft copolymers by reactive extrusion," *Prog. Polym. Sci.* 24: 81-142 (1999).

International Search Report for International Patent Application No. PCT/CA2005/001683.

Written Opinion for International Patent Application No. PCT/CA2005/001683.

Extended European Search Report for European Patent Application No. 05810143.7, Jul. 29, 2009.

European Communication, Nov. 13, 2009.

* cited by examiner

Figure 1: FT-IR spectra of PP (top), PP-g-TATM (middle), and PP-g-TATM-TAEA (bottom)

FUNCTIONALISED POLYOLEFINS, MOISTURE CURABLE POLYOLEFIN RESINS AND PROCESSES OF MANUFACTURER THEREOF

CROSS-REFERENCE TO RELATED APPLICATION

The present application claims the benefit under 35 U.S.C. §119(e) of provisional patent application Ser. No. 60/625,594, filed Nov. 8, 2004, the contents of which are hereby incorporated by reference.

BACKGROUND OF THE INVENTION

1. Field of the Invention

In one of its aspects, the present invention relates to a process for preparing a functionalised polyolefin, preferably via free radical chemistry. In another one of its aspects, the present invention relates to a functionalised polyolefin. In yet another one of its aspects, the present invention relates to a moisture curable polyolefin resin, particularly such a resin that bonds covalently to siliceous particulate material (e.g., fibers).

2. Description of the Prior Art

Polyolefin composites and blends have many applications. Of particular commercial interest are composites and blends of polypropylene, ethylene-propylene copolymers and polyisobutylene. Polypropylene, for example, is the material of choice in many packaging and automotive applications.

In recent years, there has been interest in functionalizing polymers with a view to improving and/or optimizing the chemical and/or physical properties of the base polymer with respect to its intended use.

The introduction of reactive and/or polar functional groups to polyolefins (a process referred to herein as "modifying") can greatly enhance the chemical and physical properties of the resulting polymer and its compounds. It is therefore advantageous to have cost-effective methods to introduce moieties such as anhydride, ester, amide, urethane, hydroxyl, amino, ether, silyl-ether, epoxide and alkoxysilane groups to conventional polyolefins.

Radical-mediated polymer modification using maleic anhydride, vinylsilanes and acrylate monomers is a conventional method for preparing functionalised commodity materials. However, these radical-mediated modifications typically have some adverse consequences particularly with regard to higher molecular weight polyolefins.

Specifically, when the polyolefin is polypropylene, polyisobutylene or the like, the free-radical chemistry used to graft these types of functionality can result in significant reductions in the molecular weight of the polyolefins. The resulting modified polyolefin product can have reduced viscosity and relatively poor mechanical properties, rendering it unsuitable for many industrial applications.

For example, free-radical graft-modified polypropylene and/or polyisobutylene resins have low viscosities, and are unsuitable for many industrial applications. While commercially available graft modified polypropylene resins are used as compatibilization agents for polymer blends and composites, the low molecular weight of these materials (a corollary of the fragmentation process) precludes their use in many consumer goods. Additionally, the mechanical properties of the resin also can be significantly diminished by the grafting process.

Thus, conventional approaches of radical-mediated modification of polyolefins result in alteration of the molecular weight of the polymer (i.e., decrease in molecular weight for polyolefins). This leads to a correspondingly altered viscosity of the polymer product which significantly reduces the scope of useful applications thereof.

Known strategies to minimize the effects of or degree of fragmentation and radical combination are: careful selection of starting resin and careful control of reagent concentrations. However, these methods, whether alone or in combination, do not limit the extent of fragmentation to a satisfactory level.

It is known to modify a polybutene containing a terminal double bond with an organic thiol. For example, European patent 0,342,792B teaches reacting a polybutene containing carbon-carbon double bonds with an organic thiol to form a polybutene having a thioether function. The patent teaches performing this reaction under free-radical conditions, and that it may be performed in the absence of solvent. However, the reaction taught is limited to polybutenes having a molecular weight ranging from 200 to 10,000, preferably from 400 to 2500. The description teaches that use of a polybutene of too low a molecular weight results in an addition product of relatively high volatility, while a polybutene of too high a molecular weight results in an addition reaction of low yield.

"Functional Polypropylene Blend Compatibilizers", Markomol. Chem, Macromol. Symp. 48/49, 317-332 (1991) [Mülhaupt et al. (Mülhaupt)] teaches a range of monofunctional polypropylenes containing functional endgroups, including sulfides, derived from mono-olefin-terminated polypropylene. Mülhaupt teaches a process of forming sulfide-terminated polypropylene having average molecular weight of about 900. However, Mülhaupt notes that, while free radical induced addition reactions have been carried out successfully using thiol compounds, the double bond conversion is frequently incomplete. Thus, the process taught by Mülhaupt fails to achieve 100% gelation and quantitative binding of the modified polymer to a siliceous particulate material.

While European patent 0,342,792B and Mülhaupt teach reacting low molecular weight polybutene or polypropylene with a thiol, this method has not been applied to higher molecular weight polyolefins such as polyethylene. Further, neither of these references teaches or suggests a functionalized polyolefin that may be moisture cured.

Higher molecular weight polymer resins are advantageously capable of being moisture-cured. Practically, to achieve a suitable graft content, a minimum molecular-weight of about 10,000 is needed so that the resulting polymer resin is capable of being moisture-cured. For the purpose of various applications, these moisture-curable polymer resins are advantageously bound to siliceous fillers. Gelling of these polymer resins containing siliceous fillers similarly requires a minimum molecular-weight of about 10,000. However, as a result of the molecular weight degradation associated with known radical modification of polypropylene (discussed above), the production of a moisture-curable polypropylene having a practical molecular weight based on such resins is not known.

Thus, despite the advances made in the art, there exists a need for functionalised polyolefin derivatives of high molecular weight polymers that can be produced via radical chemistry such that the molecular weight of the functionalised polyolefin derivative does not significantly change (via degradation or increase) during production thereof. More particularly, it would be highly desirable to be able to modify or functionalize a polyolefin without a consequential significant alteration of the molecular weight of the resulting polymer. Specifically, it would be highly desirable to be able to modify or functionalize a polyolefin without a consequential significant reduction in the molecular weight of the resulting polymer.

SUMMARY OF THE INVENTION

It is an object of the present invention to obviate or mitigate at least one of the above-mentioned disadvantages of the prior art.

It is a further object of the invention to provide a novel moisture curable polyolefin resin.

It is an object of the invention to provide a novel process for preparing a functionalised polyolefin.

Accordingly, in one of its aspects, the present invention relates to a process for preparing a functionalised polyolefin, comprising the step of reacting: (i) a polyolefin, (ii) a compound containing a functional group, and (iii) a coagent compound having Formula I:

wherein:
Y is a core moiety;
Z is a moiety containing at least one carbon-carbon double bond;
X is a moiety different than Z and the bond between X and Y may be a single bond or a double bond;
n is a whole number greater than or equal to 0;
m is a whole number greater than or equal to 2; and
m+n equals a number up to the valence of Y;
wherein: (a) when m is 2 and n is 0, the process comprises initially reacting the polyolefin and the coagent to form a product that is then reacted with the compound containing the functional group, and (b) the compound containing a functional group is substantially inert in free radical-mediated polymerization reactions and in free radical-mediated grafting reactions.

In another aspect, the present invention relates to a process as above wherein Z is a moiety containing at least one carbon-carbon triple bond. In another aspect, the present invention relates to a process as above wherein Z is a moiety containing at least one double bond and at least one triple bond.

In another of its aspects, the present invention relates to a functionalized polymer produced by such a process.

In another of its aspects, the present invention relates to a process for production of an adduct comprising the step of reacting a compound containing a functional group with a coagent compound having Formula I:

wherein:
Y is a core moiety;
Z is a moiety containing a carbon-carbon double bond;
X is a moiety different than Z and the bond between X and Y may be a single bond or a double bond;
n is a whole number greater than or equal to 0;
m is a whole number having a value of at least 3; and
m+n equals a number up to the valence of Y;
wherein the compound containing a functional group is substantially inert in free radical-mediated polymerization reactions and in free radical-mediated grafting reactions.

In another aspect, the present invention relates to a process as above wherein Z is a moiety containing at least one carbon-carbon triple bond. In another aspect, the present invention relates to a process as above wherein Z is a moiety containing at least one double bond and at least one triple bond.

In yet another of its aspects the present invention relates to an adduct produced by such a process.

Thus, the present inventors have surprisingly and unexpectedly discovered that polyolefins, particularly high molecular weight polyolefins (Mn>10,000) can be extensively modified with functional groups (e.g., thiols, epoxides, anhydrides, carboxylic acids, amines, amides, boron-containing compounds, silicon-containing compounds, cyano-containing compounds, sulfates, sulfonates, sulfites, esters, thioesters, dithioesters, ether, halides, phosphates, phosphonates, phosphines, phosphites and other compounds containing polar moieties) without substantially altering molecular weight (Mn), by reactions of the unsaturation in the polymer with assistance from one or more coagent compounds as described herein. This may be achieved using a compound containing a functional group, wherein the compound is substantially inert in free radical-mediated polymerization reactions and in free radical-mediated grafting reactions. Thus, those of skill in the art will recognized that such a compound excludes maleic anhydride, polymerizable olefins such as acrylates (e.g., DBBA) and the like.

Throughout this specification, reference is made to production of a functionalised polyolefin without substantially altering the molecular weight (Mn) of the starting polyolefin. It should be appreciated that the substantially unaltered molecular weight (Mn) is characterized by a substantially stable or unaltered melt viscosity of the functionalised polyolefin as compared to the starting polyolefin.

The choice of functional groups and of the compounds which contribute such functional groups may be selected by a person of ordinary skill in the art depending on the particular application for the modified polymer. The functional group may be introduced in an olefin derivation reaction. Olefin derivatization reactions in general fall into two broad categories: (i) addition reactions and (ii) substitution reactions. Non-limiting examples of addition reactions that may be improved using the present invention include: hydration, hydrogenation, halohydrin formation, dimerization, alkylation, polymerization, hydroxylation, halogenation, addition of free radicals, addition of carbenes and addition of sulfuric acid. Non-limiting examples of substitution reactions that may be improved using the present invention include: allylic substitution, ozonolysis and halogenation. The reagents typically used in these reactions would be known to those of skill in the art.

Thus, the present invention is capable of improving reactions that are commonly performed with polyolefins, such as polypropylene. Common reactions of polypropylene are discussed in Mulhaupt, R et al., "Functional Polypropylene Blend Compatibilizers," *Makromol. Chem., Macromol. Symp.* 48/49, 317-332 (1991), for example, the reaction of polypropylene by epoxidation, Alder-ene addition, hydrosilylation and thiol-ene addition.

Preferred olefin derivatization reactions that may be improved using the present invention include: thiol-ene addition, Alder-ene addition, cycloaddition, hydrosilylation, epoxidation and hydroboration.

Still further, the present inventors have surprisingly and unexpectedly discovered that a polyolefin can be functionalised through a process involving reacting the polyolefin with a coagent compound as described herein and a compound containing a functional group (e.g., thiols, epoxides, anhydrides, carboxylic acids, amines, amides, boron-containing compounds, silicon-containing compounds, cyano-containing compounds, sulfates, sulfonates, sulfites, esters, thioesters, dithioesters, ether, halides, phosphates, phosphonates, phosphines, phosphites, olefins and other compounds containing polar moieties) which compound is substantially inert in free radical-mediated polymerization reactions and in free radical-mediated grafting reactions. The process can be carried out by initially contacting the polyolefin with the coagent compound and then contacting the product thereof with the compound containing a functional group. Alternatively, it is possible initially to form an adduct of the coagent compound and the compound containing a functional group, and thereafter contact the adduct with the polyolefin. One or both of the coagent compound and the compound containing a functional group may optionally comprise a spacer moiety that has the effect of relatively increasing the physical separation between the functional group and the coagent compound (i.e., the reactive moiety thereof), and/or the coagent compound (i.e., the reactive moiety thereof) and the polyolefin.

Many applications for the present polyolefin resins will be apparent to a person skilled in the art. For example, using the present invention, it is possible to produce a moisture-curable polyolefin resin that has a relatively high molecular weight (e.g., M.W.>10,000). Moisture-curable polypropylene, for example, could be used in such diverse application as radiant floor heating systems, pipeline coatings, heat-shrinking products, fiber-reinforced composite materials and the like.

BRIEF DESCRIPTION OF THE DRAWINGS

Embodiments of the present invention will be described with reference to the accompanying drawings, in which.

DETAILED DESCRIPTION OF THE PREFERRED EMBODIMENTS

The present invention includes functionalised polyolefins, moisture curable polyolefin resins, and a process of manufacturing both of these products.

The process of the present invention can introduce desirable functionality to higher molecular weight polyolefins with minimal or no significant change in the molecular weight (Mn) of the starting polymer.

In one embodiment, the invention involves a process for preparing a functionalised polyolefin, comprising the step of reacting: (i) a polyolefin, (ii) a compound containing a functional group, and (iii) a coagent compound having Formula I:

$$X_n\text{—}Y\text{—}Z_m \quad (I)$$

wherein:
Y is a core moiety;
Z is a moiety containing a carbon-carbon double bond;
X is a moiety different than Z and the bond between X and Y may be a single bond or a double bond;
n is a whole number greater than or equal to 0;
m is a whole number greater than or equal to 2; and
m+n equals a number up to the valence of Y;
wherein: (a) when m is 2 and n is 0, the process comprises initially reacting the polyolefin and the coagent to form a product that is then reacted with the compound containing the functional group, and (b) the compound containing a functional group is substantially inert in free radical-mediated polymerization reactions and in free radical-mediated grafting reactions.

Preferably, the polyolefin and the coagent are miscible with each other and/or with a common solvent. More preferably, the polyolefin and coagent are miscible with each other such that the process can be occur as a single-phase or homogeneous system, which provides the advantage that there is no additional subsequent step needed to eliminate a solvent.

In another embodiment, the present invention involves a process as above wherein Z is a moiety containing at least one carbon-carbon triple bond. In another embodiment, the present invention involves a process as above wherein Z is a moiety containing at least one double bond and at least one triple bond.

The compound of Formula I contains 2 or more Z moieties. It should be clearly understood that these Z moieties may be the same or different. Further, if the compound of Formula I contains 2 or more X moieties, these X moieties may be the same or different.

Throughout this specification, reference will be made to hydrocarbon moieties that may be "substituted or unsubstituted". It is intended that this term encompass hydrocarbon moieties that are optionally substituted with one or more substituents or may be modified to include one or more substituents, wherein a substituent is selected from the group consisting of aliphatic, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphate ester, phosphonato, phosphinato, cyano, amino, acylamino, amide, imino, sulfhydryl, alkylthio, arylthio, thiocarboxylate, dithiocarboxylate, sulfate, sulfonato, sulfamoyl, sulfonamido, nitro, nitrile, trifluoromethyl, azido, heterocyclyl, aromatic, and heteroaromatic moieties, ether, epoxide, ester, anhydride, boron-containing moieties, silicon-containing moieties and combinations of any of these.

Further, throughout this specification, reference is made to an "aliphatic" moiety. It is intended that this term encompass hydrocarbon moieties that are straight chain, branched or cyclic and, further, the aliphatic moiety may be substituted or unsubstituted.

Thus, the coagent compound has at least two carbon-carbon double bonds, or two carbon-carbon triple bonds, or a carbon-carbon double bond and a carbon-carbon triple bond, which may be substituted. However, the number of carbon-carbon double and/or triple bonds (above two) is not particularly restricted. Preferably, the coagent compound has between two and four moieties that contain a carbon to carbon double bond.

Y is a core moiety and may be inorganic and/or organic (e.g., an organometallic moiety is an example of a moiety that is both inorganic and organic). Preferably, the core moiety is not reactive, so as to stabilize a grafted intermediate produced in the method from fragmenting.

Thus, in one embodiment, Y may be an inorganic moiety. For example, Y may be a main group polyvalent element selected from the Periodic Table of Elements. Preferably, Y is an element selected from any one of Groups IIIa, IVa and Va of the Periodic Table. Non-limiting examples of suitable such elements include silicon and phosphorus.

In another embodiment, Y may be an organic moiety. In a preferred embodiment, the organic moiety comprises a substituted or unsubstituted $C_1$-$C_{10}$ alkyl moiety, more preferably a substituted or unsubstituted $C_1$-$C_4$ alkyl moiety, most preferably a $C_1$ alkyl moiety. In another preferred embodiment, the organic moiety comprises a substituted or unsubstituted $C_5$-$C_{20}$ aryl moiety, more preferably a substituted or unsubstituted $C_6$-$C_{10}$ aryl moiety, even more preferably a substituted or unsubstituted phenyl moiety, most preferably (unsubstituted) phenyl.

As stated above, m+n equals a number up to the valence of Y. Given that Y may be an organic and/or inorganic moiety, the use of the term "valence" is intended to have a broad meaning. For example, if Y is a benzene ring, those of skill in the art will recognize that, in the context of the present invention, benzene has a "valence" of 6.

In Formula I, Z is a moiety containing a carbon-carbon double bond or a carbon-carbon triple bond. Preferably, the carbon-carbon double bond is a terminal carbon-carbon double bond. More preferably, the carbon-carbon double bond (terminal or internal) is activated by a heteroatom such as oxygen or sulfur, most preferably oxygen. Thus, such activation can be achieve via an ether moiety, an acrylate moiety, an ester moiety, carbonyl moiety or the like. Preferably, Z is a $C_2$-$C_{20}$ moiety having the above characteristics.

The choice for X in the compound of Formula I is not particularly restricted. For example X may be a hydrocarbon moiety such as a substituted or unsubstituted $C_1$-$C_{20}$ aliphatic moiety or a substituted or unsubstituted $C_5$-$C_{20}$ aryl moiety.

In one preferred embodiment, X comprises an $sp^2$-hybridized moiety, such as oxygen.

In another preferred embodiment, X comprises a substituted or unsubstituted $C_1$-$C_{15}$ aliphatic moiety, more preferably a substituted or unsubstituted $C_1$-$C_6$ aliphatic moiety. The aliphatic moiety may contain one or more heteroatoms. A non-limiting example of an aliphatic moiety is one that contains a hydroxy group.

In a more preferred embodiment of the present process, the coagent is selected from the group comprising a polyallyl compound, a polyacrylate compound, a polyvinyl compound and mixtures thereof.

Preferably, the polyallyl compound is selected from the group comprising triallyl trimellitate (TATM), triallyl phosphate (TAP), pentaerythritol diallyl ether (PE(Di)AE), pentaerythritol triallyl ether (PE(Tri)AE), pentaerythritol tetraallyl ether (PE(Tetra)AE), 1,3,5-triallylmesate, triallyl cyanurate and mixtures thereof. More preferably, the polyallyl compound is selected from the group comprising triallyl trimellitate (TATM), 1,3,5-triallylmesate and mixtures thereof.

Preferably, the polyacrylate compound is selected from the group comprising pentaerythritol diacrylate (PE(Di)A), pentaerythritol triacrylate (PE(Tri)A), pentaerythritol tetraacrylate (PE(Tetra)A) and mixtures thereof. More preferably, the polyacrylate compound comprises pentaerythritol tetraacrylate (PE(Tetra)A).

Preferably, the polyvinyl compound is selected from the group comprising natural polyunsaturated oil, divinylbenzene and mixtures thereof. More preferably, the polyvinyl compound comprises divinylbenzene.

The polyolefins suitable for the present invention are not particularly restricted, and the selection of a suitable polyolefin is within the purview of a person skilled in the art.

As used through this specification, the term "polyolefin" is intended to have a broad meaning and encompasses homopolymers, copolymers, terpolymers, etc. which are derived from the polymerization of at least one olefin monomer.

As used throughout this specification, the term "olefin monomer" is intended to have a broad meaning and encompasses α-olefin monomers, diolefin monomers and polymerizable monomers containing at least one internal olefin linkage.

In a preferred embodiment, the olefin monomer is an α-olefin monomer. α-Olefin monomers are well known in the art and the choice thereof for use in the present process is within the purview of a person skilled in the art. Preferably, the α-olefin monomer is selected from the group comprising propylene, 1-butene, isobutene, 1-pentene, 1-hexene, 1-octene, branched isomers thereof, styrene, α-methylstyrene and mixtures thereof. The most preferred α-olefin monomer is propylene.

In yet another preferred embodiment, the olefin monomer comprises a diolefin monomer. Diolefin monomers are well known in the art and the choice thereof for use in the present process is within the purview of a person skilled in the art. In one preferred embodiment, the diolefin monomer is an aliphatic compound. Non limiting examples of suitable aliphatic compounds may be selected from the group comprising 1,3-butadiene, isoprene, 2,3-dimethyl-1,3-butadiene, 2-ethyl-1,3-butadiene, piperylene, myrcene, allene, 1,2-butadiene, 1,4,9-decatrienes, 1,4-hexadiene, 1,6-octadiene, 1,5-hexadiene, 4-methyl-1,4-hexadiene, 5-methyl-1,4-hexadiene, 7-methyl-1,6-octadiene, phenylbutadiene, pentadiene and mixtures thereof. In another preferred embodiment, the diolefin monomer is an alicyclic compound. Non-limiting examples of suitable alicyclic compounds may be selected from the group comprising norbornadiene, alkyl derivatives thereof, 5-alkylidene-2-norbornene compounds, 5-alkenyl-2-norbornene compounds and mixtures thereof, such as 5-methylene-2-norbornene, 5-ethylidene-2-norbornene, 5-propenyl-2-norbornene and mixtures thereof. Further non-limiting examples of suitable alicyclic compounds may be selected from the group comprising 1,4-cyclohexadiene, 1,5-cyclooctadiene, 1,5-cyclododecadiene, methyltetrahydroindene, dicyclopentadiene, bicyclo [2.2.1]hepta-2,5-diene and mixtures thereof.

Of course it is possible to utilize mixtures of the various types of olefin monomers described hereinabove.

In one preferred embodiment, the olefin monomer is a mixture of ethylene and at least one α-olefin (as described hereinabove) which results in the production of a copolymer. The preferred such monomer mixture comprises ethylene and propylene. In this embodiment, it is preferred to utilize a mixture comprising from about 30 to about 75, more preferably from about 35 to about 65, weight percent ethylene and from about 25 to about 70, more preferably from about 35 to about 65, weight percent α-olefin.

In another preferred embodiment, the olefin is a mixture of ethylene, at least one α-olefin (as described hereinabove) and at least one diolefin monomer (as described hereinabove) which results in the production of a terpolymer. The preferred such monomer mixture comprises ethylene, propylene and one or both of 5-ethylidene-2-norbornene and 1,5-hexadiene. In this embodiment, it is preferred to incorporate into the preferred mixture of ethylene and α-olefin from about 0.5 to about 15, more preferably from about 1 to about 10, weight percent of the diolefin monomer.

The more preferred polyolefins may be selected from the group consisting of polypropylene, polyethylene, ethylene-propylene copolymers, polyisobutylene and blends of two or more of these polyolefins. The most preferred polyolefin is polypropylene.

The polyolefin materials used in the present process are commercially available and may be readily produced using free radical, Ziegler-Natta and/or metallocene polymerization techniques and the like.

Preferably the polyolefins used in the present process have a molecular weight (Mn) in the range from about 10,000 to about 500,000, more preferably from about 10,000 to about 100,000, even more preferably from about 20,000 to about 80,000, and most preferably from about 40,000 to about 60,000 Daltons. It will be understood by those of skill in the art that reference to molecular weight refers to a population of polymer molecules and not necessarily to a single or particular polymer molecule.

The present inventors have discovered that the use of one or more coagent compounds as described herein facilitates high-yield olefin derivatizations that do not significantly affect molecular weight. For example, conventional thiol-ene addition to a high molecular weight polyolefin is inefficient, but, for example, treatment of the polyolefin with a coagent compound as described herein, followed by thiol addition improves the yield dramatically, and produces a functionalised polyolefin of stable melt viscosity.

An aspect of the present invention also relates to further reaction of the bound coagents. In particular, esters and phosphate esters will undergo substitution reactions with a wide range of nucleophiles. Thus, by grafting the coagent compound to the polyolefin, ionic reactions can be performed on the bound coagent moiety to generate functional derivatives of stable melt viscosity. Embodiments of this are illustrated in the Examples hereinbelow.

Thus, an aspect of the present process involves using a coagent compound, such as polyallyl compound, to introduce functionality, preferably using radical chemistry. Surprisingly, the inventors of the present invention found that, for example, functional polyallyl-containing compounds, functional polyacrylate-containing compounds and functional polyvinyl-containing compounds (by "functional" is meant adduct of the coagent compound and the compound containing a functional group discussed above) can be grafted to a polyolefin, such as polypropylene, without deleteriously altering melt viscosity. The process can similarly be used to introduce any number of functional groups in a controlled manner. Suitable compounds for introducing the functional groups are discussed below.

A non-limiting example of a suitable polyallyl adduct is bisallylsulfide, a structural isomer of which has the following formula:

Another suitable polyallyl adduct is bisallylepoxide, a structural isomer of which has the following formula:

Further, the alkoxysilane functionality introduced by this grafting process can be activated subsequently using conventional moisture-curing techniques. When the polyolefin is polypropylene, the product is a moisture-curable polypropylene resin that is capable of bonding to siliceous fillers.

Those of skill in the art will recognize that the bisallylsulfide and the bisallylepoxide exemplified above are adducts that contain both a polyallyl moiety and a functional group. Of course, other functional groups may be added to a polyallyl compound to produce different adducts. Similarly, coagent compounds other than polyallyl compounds may be used to produce a suitable adduct.

Non-limiting examples of compounds containing a functional group may be selected from the group comprising thiols, epoxides, anhydrides, carboxylic acids, amines, amides, boron-containing compounds, silicon-containing compounds, cyano-containing compounds, sulfates, sulfonates, sulfites, esters, thioesters, dithioesters, ether, halides, phosphates, phosphonates, phosphines, phosphites, other compounds containing polar moieties and mixtures thereof. Preferably, the compound containing a functional group is selected from the group consisting of silanes, epoxides, anhydrides and mixtures thereof.

The present process may be carried out in a single batch method or successive batch methods. Thus, it is possible to combine in a single reaction vessel the polyolefin, the compound containing the functional group and the coagent compound (i.e., except in the case where m is 2 and n is 0 in the compound of Formula I) to produce the present functionalised polyolefin. Alternatively, it is possible to react the compound containing the functional group with the coagent compound in a reaction vessel to produce an adduct and thereafter react the adduct (in the same reaction vessel or a different reaction vessel) with the polyolefin to produce the present functionalised polyolefin. In the case where m is 2 and n is 0 in the compound in the compound of Formula I, the coagent compound may be initially reacted with the polyolefin in a reaction vessel to form an intermediate product that is thereafter reacted (in the same reaction vessel or a different reaction vessel) with the compound containing a functional group to produce the present functionalised polyolefin.

As an example of the flexibility of present process, instead of adding the bisallyl sulfide shown above to generate moisture curable polypropylene, a triallyl compound having the formula:

can be added to polyolefin (e.g., polypropylene) before introducing the alkoxysilane functionality by reacting the treated polymer with a functional thiol or one of the other compounds containing a functional group exemplified above. As discussed above, a coagent compound other than the above triallyl compound may be added to the polyolefin. While the process steps may be performed in a single batch method, for some functional groups, such as amines, a sequential method is preferable.

While the process of the present invention utilizes a compound having at least one functional group, the number of functional groups introduced is not restricted and is within the purview of the worker skilled in the art. Preferably, the compound having at least one functional group has a molecular weight of less than about 5,000 and is soluble in an organic solvent.

The present invention further includes a moisture-curable olefin resin. The preferred moisture-curable olefin resin is a commercial grade of isotactic polypropylene. This moisture-curable resin may be bound covalently to siliceous particulate materials or fillers (e.g., silicates containing silicon and oxygen such as glass fibres, silica powders, clays and the like). This resin may also be crosslinked via moisture-curing to create a thermosetting material.

Conventional graft-modifications of ethylene-rich polymers do not reduce the molecular weight, as is the case for polypropylene. Rather, radical combination is the dominant molecular weight-altering event for this substrate, and the thiol-ene approach is designed to yield moisture-curable resins without incurring crosslinking. Moisture-curable HDPE-g-MPTMS [i.e., High Density PolyEthylene-graft-mercaptopropyl trimethoxysilane] derivatives of stable melt flow index (MFI) can be prepared using this process.

While not wishing to be bound by any particular theory or mode of action, it is believed that the present process involves the generation of free-radicals in the reaction mixture in order to initiate the process. Free-radicals may, for example, be generated through the use of ultraviolet light, a chemical initiator (such as a peroxide), thermo-mechanical means, radiation, electron bombardment and the like. See any of the following references for a general discussion on radical generation techniques: Moad, G. *Prog. Polym. Sci.* 1999, 24, 81-142; Russell, K. E. *Prog. Polym. Sci.* 2002, 27, 1007-1038; and Lazar, M., *Adv. Polym. Sci.* 1989, 5, 149-223.

Embodiments of the present invention will be described with reference to the following Examples, which are provided for illustrative purposes only and should not be used to limit or construe the scope of the invention.

EXAMPLE 1

In this Example, isotactic polypropylene pellets (i-polypropylene, $M_n$=50,000, polydispersity=3.8, Sigma-Aldrich) (45 g) and the amount of triallyl trimellitate (TATM) shown in Table 1 were mixed at 180° C. and 60 rpm within a Haake Polylab R600 internal batch mixer for 1 minute. The amount of dicumylperoxide (DCP) shown in Table 1 was then added, and the mixing was continued for a further 15 minutes, yielding i-polypropylene-g-TATM.

The extent of TATM addition was determined by an FT-IR method. i-Polypropylene-g-TATM (1 g) was purified by dissolved in boiling xylenes (15 mL) and precipitated from solution using acetone (80 mL). The purified resin was dried under vacuum, and thin films of the material were analyzed using a Nicolet Avatar 360 FT-IR ESP spectrometer. The bound TATM content was determined from the area derived from the 1305-1704 $cm^{-1}$ resonance of the coagent relative to the 420-500 $cm^{-1}$ internal standard region originating from the resin. Comparison of the ratio of these areas to calibration mixtures provided the TATM grafted values listed in Table 1.

i-Polypropylene-g-TATM was further modified by reaction with 3-mercaptopropyl trimethoxysilane (MPTMS, 95%, Sigma-Aldrich). Ground i-polypropylene-g-TATM. (0.75 g) was coated with a chloroform solution containing 2,5-dimethyl-2,5-di(t-butylperoxyl)hexane (L-101, Elf Atochem) (0.1 wt %) and MPTMS (3.9 wt %). The chloroform was evaporated from the sample, and the resulting mixture was charged to the cavity of an Atlas Laboratory Mixing Molder at 170° C. for 15 minutes, yielding i-polypropylene-g-TATM/MPTMS.

The extent of MPTMS addition to i-polypropylene-g-TATM was determined by moisture-curing the functionalized resin, and by coupling the modified polymer to precipitated silica. Since only those polymer chains that contain silane functionality can engage in these reactions, moisture-curing and silica binding yields are effective measures of the extent of MPMTS grafting to the i-polypropylene substrate. These reactions were conducted in the following manner.

i-Polypropylene-g-TATM/MPTMS (1.0 g) and xylenes (20 mL) were heated to reflux prior to the addition of dibutyltin dilaurate (10 μL, 20.2 μmol) and water (0.5 μL). The mixture was maintained at a reflux condition for 20 minutes, after which the polymer was recovered from solution by precipitation with acetone (150 mL) and dried in vacuo. Gel content was determined by extracting cured products with refluxing xylenes from 120 mesh sieve cloth. Extraction solutions were stabilized with 100 ppm of 2,6-di-t-butyl-4-methylphenol (BHT), and the procedure was conducted for a minimum of 2 hours, with longer times having no effect on the results. Unextracted material was dried under vacuum to constant weight, and gel content was calculated as the weight percent of insoluble polymer—the results are reported in Table 1.

i-Polypropylene-g-TATM/MPTMS (1.0 g), xylenes (20 mL) and precipitated silica (0.4 g) were heated to reflux for 30 minutes, after which the polymer and silica were recovered from solution by precipitation with acetone (150 mL) and dried in vacuo. Gel content was determined as described above, with the data presented as weight percent of insoluble polymer after correcting for the silica content of the sample— the results are reported in Table 1.

Melt flow rate (MFR) values are reported as grams of resin extruded in 10 minutes, as determined using a Tinius Olsen apparatus at 230° C. with a 2.16 kg load—the results are reported in Table 1.

This approach uses additives to offset the extent of molecular weight losses during conventional peroxide mediated i-polypropylene degradation. Generally, polyallyl compounds in combination with small amounts of peroxide can increase the unsaturation content of the material without significantly changing melt viscosity.

The data presented in Table 1 show that this approach is effective. Small amounts of TATM stabilize the MFR of the resin when included in the degradation process. Of equal importance is the relatively small amount of MPTMS needed to provide acceptable moisture-cure gel contents and bound polymer yields. Just 3.9 wt % of MPTMS was needed to produce i-polypropylene-g-TATM/MPTMS with a stable MFR that moisture cured to 91% gel content. This combination of high gel content, stable melt viscosity, and low thiol requirements cannot be matched by conventional degradation pretreatments (See Example 2 below) or by standard thiolene additions (See Example 3 below).

EXAMPLE 2

This is a comparative Example in which the TATM used in Example 1 was omitted. Radical-mediated i-polypropylene degradations, and subsequent MPTMS additions were conducted as described above in Example 1, using the formulations and reaction conditions listed in Table 2.

The MFR of i-polypropylene degradation products derived from the two approaches were compared. The degradation of i-polypropylene in the absence of TATM resulted in severe losses to melt viscosity, as revealed by MFR values of 220 g/10 min when 0.05 wt % DCP was used, and greater than 300 g/10 min when 0.10 wt % was employed (Table 2). In contrast, i-polypropylene degradations that included 1.0 wt %

TATM yielded product MFR values of just 42 g/10 min and 37 g/min under equivalent reaction conditions.

EXAMPLE 3

This is a comparative Example in which no radical-mediated coagent treatment of i-polypropylene is performed prior to the thiol-ene addition of MPTMS. Table 3 provides the MFR, moisture-curing yield and bound polymer yield recorded using the materials and methods described in Example 1. The thiol-ene addition generated i-polypropylene-g-MPTMS with a stable melt viscosity, as indicated by an MFR of 37 g/10 min. However, the yield of moisture-curing and silica binding was less than those recorded for i-polypropylene-g-TATM/MPTMS (Table 1).

EXAMPLE 4

It was demonstrated that thiol-ene derivatizations of polypropylene-based polymers were improved through the use of polyallyl modifiers. A sequential polypropylene-degradation/thiol addition process using TATM in the first step and MPTMS in a second step has proven to be successful in generating curable derivatives of stable viscosity. The high levels of TATM incorporation recorded in these degradation reactions suggest that a functional polyallyl compound could be used in a one-step modification process.

The bisallyl sulfide (BAS) shown below was used to illustrate this concept. To prepare this reagent, TATM (1 g), MPTMS (0.60 g) and 2,2'-azobisisobutyronitrile (0.001 g) were combined in a round-bottom flask under a nitrogen atmosphere. The resulting solution was heated to 90° C. for 1 hour. Residual reactants were removed by vacuum distillation, and the residue was analyzed by $^1$H-NMR spectroscopy, which confirmed that one in three allyl groups of TATM were converted to the desired sulfide functionality.

Structure of the TATM+MPTMS Adduct (BAS) used for Polypropylene-Modification (One of Three Structural Isomers)

Ground i-polypropylene (0.75 g) was coated with a chloroform solution containing 2,5-dimethyl-2,5-di(t-butylperoxyl)hexane (L-101, Elf Atochem) (0.1 wt %) and the required amount of BAS. The chloroform was evaporated from the sample, and the resulting mixture was charged to the cavity of an Atlas Laboratory Mixing Molder at 170° C. for 15 minutes, yielding i-polypropylene-g-BAS. The data presented in Table 4 provides evidence of the utility of this approach. The modified polymers possessed a stable MFR, and cured to high gel contents.

This method used a functional adduct that is produced by radical-mediated thiolene addition prior to the polypropylene grafting process. It is possible, however, to add TATM, MPTMS and peroxide to polypropylene directly to a reactive compounding process. This reaction was conducted using the methodology presented above for BAS grafting to i-polypropylene. The bisallyl adduct is prepared in situ by this approach, and its addition to the polymer results in acceptable gel contents, as revealed by the last reaction summarized in Table 4.

EXAMPLE 5

In this Example, three other polyunsaturated compounds are shown to stabilize the MFR of polypropylene during radical-mediated degradation, thereby making the polymer more amenable to an olefin derivatization process such as thiol-ene addition. Pentaerythritol triallyl ether (PE(Tri)AE) and triallyl phosphate (TAP) both contain allylic carbon-carbon double bonds, but they differ from TATM in that they are allylic ethers. The latter coagent compound, TAP, also differs from TATM in that it is based on a phosphate core. The structure of pentaerythritol triacrylate (PE(Tri)A) is significantly different from the polyallyl series that includes TATM, PE(Tri)AE and TAP, since the reactive olefinic group within PE(Tri)A is an acrylate functionality.

Table 5 summarizes experiments wherein triallyl phosphate (TAP), pentaerythritol triallyl ether (PE(Tri)AE) or pentaerythritol triacrylate (PE(Tri)A) was included in an i-PP degradation formulation, prior to the addition of MTPMS. The polymer modification procedures and product analyses used in this Example are those presented in Example 1. The data show that despite the structural differences of these three coagents, they stabilized the MFR of i-PP when the resin was exposed to active peroxide. Furthermore, subsequent thiol-ene additions resulted in moisture-curing and silica-binding yields that approached those recorded for the TATM system.

EXAMPLE 6

In this Example, thiol-ene addition of MPTMS to a high density polyethylene homopolymer (HDPE, Sclair 2907, Nova Chemicals) is illustrated. The methods used to prepare HDPE-g-MPTMS have been described in Example 1, using the formulations listed in Table 6.

Conventional graft-modifications of ethylene-rich polymers do not reduce the molecular weight, as is the case for polypropylene. Rather, radical combination is the dominant molecular weight-altering event for this substrate, and the thiol-ene approach is designed to yield moisture-curable resins without incurring crosslinking. As shown in Table 6, moisture-curing HDPE-g-MPTMS derivatives of stable melt flow index (MFI) were prepared.

EXAMPLE 7

In this Example, a one-step addition of a bisallyl epoxide (BAE, shown below) to i-polypropylene is illustrated. This reagent was prepared by adding to a solution of m-chloroperbenzoic acid (0.34 g) and chloroform (7 mL) a solution of triallyl trimellitate (0.67 g) and chloroform (5 mL) in a dropwise fashion. The mixture was stirred at room temperature for 12 hours, then washed with a 10% aqueous solution of NaHCO$_3$, and dried over anhydrous CaSO$_4$. Chloroform was then removed by rotary evaporation, and the product was characterized by $^1$H-NMR analysis, which confirmed that, on average, BAE contained two allylic ester groups and one expoxide group per molecule.

Structure of the Epoxidized TATM Adduct (BAE) used for Polypropylene-Modification (One of Three Structural Isomers)

The radical-mediated addition of BAE to i-polypropylene was accomplished using the methods described in Example 1. i-Polypropylene (1.4 g), DCP (0.001 g) and BAE (0.09 g) were included in the grafting formulation, which was subjected to 170° C. for 7 minutes in an Atlas Laboratory mini-mixer, yielding i-polypropylene-g-BAE. The material was purified in the manner described for i-polypropylene-g-TATM, and the presence of approximately 2.2 wt % of bound BAE was confirmed by FT-IR analysis.

EXAMPLE 8

In this Example, the one-step modification of polyisobutylene (PIB, $M_n$ =400,000) with the bisallyl sulfide reagent described in Example 3 is illustrated. PIB (1.0 g) and bisallyl sulfide (0.05 g) were mixed at 160° C. for 5 minutes within a Haake Polylab batch mixer operating at 60 rpm. 3,3,5-Trimethyl-1,1-bis(t-butylperoxy)cyclohexane (L-231, Elf Atochem) (0.01 g) was then added, and mixing was continued for a further 5 minutes, yielding PIB-g-BAS.

A sample of PIB-g-BAS (1.0 g) was dissolved in toluene (20 mL), precipitated from solution with acetone (120 mL), and dried under vacuum. $^1$H-NMR analysis of this purified material revealed evidence of bound BAS, in the form of the characteristic singlet of methoxy groups at 3.5 ppm. Integration of the bound methoxy resonance relative to that of the methylene resonances derived from the backbone of PIB yielded an estimated bound BAS content of 5.4 µmoles/gram.

Changes to the viscoelastic properties of the polymer brought about by treatment with peroxide in the presence, and in the absence, of BAS were evaluated by dynamic mechanical analysis using an Advanced Polymer Analyzer 2000 from Alpha Technologies. The storage modulus (G'), loss modulus (G") and tanδ measured for unmodified PIB, PIB exposed to radical activity in the absence of BAS, and PIB-g-BAS are summarized in Table 7. A reduction in molecular weight is evident from a decline in G' and a corresponding increase of tanδ. The data show that PIB-g-BAS was prepared with a slight reduction in G'. However, the loss of molecular weight was much less than that experienced when PIB is treated with peroxide in the absence of the functional coagent. Therefore, the use of BAS mitigated the molecular weight loss associated with radical-mediated grafting, while also introducing the desired trialkoxysilane functionality.

EXAMPLE 9

Figure 1:
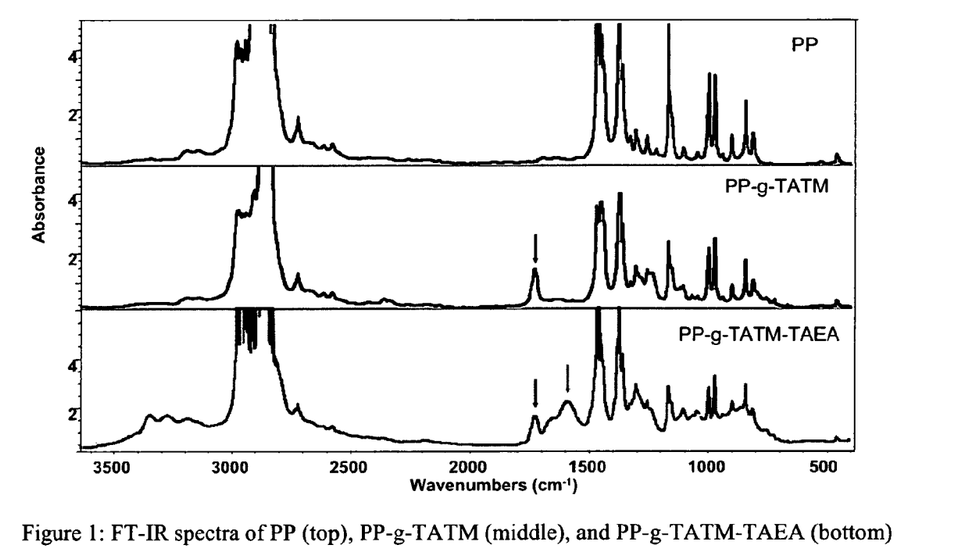
FIG. 1 illustrates FT-IR spectra of various materials used and prepared in Example 9 hereinbelow.

In this Example, the addition of TATM to i-polypropylene is followed by reaction with N(CH$_2$CH$_2$NH$_2$)$_3$, or tris(2-aminoethyl)amine (TAEA), to yield an amide derivative that contains residual amine functionality. PP-g-TATM was prepared using the methodology in Example 1, and the presence of bound ester functionality was confirmed by FT-IR analysis on a thin film of the purified polymer—see FIG. 1. Subsequently, purified PP-g-TATM (1.5 g) was combined with xylenes (17 mL), 2,6-di-tert-butyl-4-methylphenol (BHT, antioxidant, 200 ppm) and TAEA (1.25 g) and the mixture was heated to reflux for 3 hours. The polymer product was recovered by precipitation with acetone, and dried under vacuum. The FT-IR spectrum of PP-g-TATM-TAEA is illustrated in FIG. 1, which clearly shows the presence of amide functionality at 1600 cm$^{-1}$ as well as residual amine groups at 3300 cm$^{-1}$.

EXAMPLE 10

The methodology in Example 9 is repeated using the phosphate ester derivatives of polyolefins, such as those prepared in Example 5. Reaction of purified PP-g-TAP with a nucleophilic reagent such as TAEA displaces allyl alcohol, and generates a polyolefin containing residual amine functionality.

EXAMPLE 11

The methodology in Example 1 is repeated using an alkyne analogue of TATM, as illustrated below:

Reaction of this polyunsaturated coagent with polypropylene yields a polymer whose melt viscosity is not significantly different from the parent material. This material responds to MPTMS addition in a manner that is consistent with PP-g-TATM, PP-g-TAP, PP-g-PETAE, and PP-g-PETA, as demonstrated in Example 5.

EXAMPLE 12

In this Example, adducts that are useful for selective polyolefin functionalization are prepared by hydroboration and oxidation of unsaturated coagents such as triallyl trimesate (TAM).

TAM is reacted with one molar equivalent of BH$_3$ in tetrahydrofuran (THF) at 50° C. for 8 hours, followed by the slow addition of a solution of NaOH in ethanol and a solution of H$_2$O$_2$ at room temperature to produce a bisallyl alcohol having the following chemical structure:

This hydroxyl functionalized TAM derivative can be used to selectively functionalize a polyolefin, for example, using the methodology used in Examples 1 and 4-9.

EXAMPLE 13

In this Example, adducts that are useful for selective polyolefin functionalization are prepared by hydrosilylation of unsaturated coagents such as triallyl trimesate (TAM).

TAM is reacted with one molar equivalent of a trialkylsilane such as tri n-propylsilane(HSi(n-Pr)$_3$) to produce a bis-allyl silane having the following chemical structure:

This silane functionalized TAM derivative can be used to selectively functionalize a polyolefin, for example, using the methodology used in Examples 1 and 4-9.

TABLE 1

Sequential grafting of TATM and MPTMS to i-polypropylene

| | | i-PP-g-TATM[a] | | i-PP-g-TATM/MPTMS[b] | | |
|---|---|---|---|---|---|---|
| [DCP] (wt %) | [TATM] (wt %) | Product MFR (g/10 min) | Grafted TATM (wt %) | Product MFR (g/10 min) | Cured Gel Content (wt %) | Bound Polymer (wt %) |
| 0.05 | 1.0 | 37 | 0.27 | 37 | 25 | 39 |
| 0.10 | 1.0 | 42 | 0.54 | 46 | 47 | 61 |
| 0.20 | 1.0 | 45 | 0.62 | 48 | 80 | 88 |
| 0.10 | 0.5 | 41 | 0.40 | 41 | 38 | 43 |
| 0.10 | 2.0 | 36 | 0.64 | 39 | 91 | 100 |

[a]TATM grafting conditions: T = 180° C.; 15 min.
[b]Thiol addition conditions: [MPTMS] = 3.9 wt %; [L-101] = 0.1 wt %; T = 170° C.; 15 min.

TABLE 2

Sequential i-polypropylene degradation and MPTMS addition

| | | Degraded i-PP[a] | | Degraded i-PP-g-MPTMS[b] | | |
|---|---|---|---|---|---|---|
| [DCP] (wt %) | [TATM] (wt %) | Product MFR (g/10 min) | Grafted TATM (wt %) | Product MFR (g/10 min) | Cured Gel Content (wt %) | Bound Polymer (wt %) |
| 0.05 | 0.0 | 220 | — | 218 | 43 | 50 |
| 0.10 | 0.0 | >300 | — | >300 | 57 | 64 |

[a]Degradation conditions: T = 180° C.; 15 min.
[b]Thiol addition conditions: [MPTMS] = 3.9 wt %; [L-101] = 0.1 wt %; T = 170° C.; 15 min.

TABLE 3

MPTMS addition to undegraded i-polypropylene

| | | i-PP | | i-PP-g-MPTMS[a] | | |
|---|---|---|---|---|---|---|
| [DCP] (wt %) | [TATM] (wt %) | i-PP MFR (g/10 min) | Grafted TATM (wt %) | Product MFR (g/10 min) | Cured Gel Content (wt %) | Bound Polymer (wt %) |
| — | — | 35 | — | 37 | 10 | 8 |

[a]Thiol addition conditions: [MPTMS] = 3.9 wt %; [L-101] = 0.1 wt %; T = 170° C.; 15 min.

TABLE 4

TATM-MPTMS adduct (BAS) addition to i-PP[a]

| BAS Loading (wt %) | Grafted Adduct (wt %) | Product MFR (g/10 min) | Gel Content (wt %) |
|---|---|---|---|
| 0.75 | 0.54 | 34 | 25 |
| 1.50 | 0.98 | 30 | 52 |
| 3.00 | 1.52 | 24 | 66 |
| 5.00 | 1.84 | 21 | 82 |

[a][L-101] = 0.1 wt %; T = 170° C.; 15 min.

TABLE 5

Sequential grafting of unsaturated coagents and MPTMS to i-polypropylene

| Coagent[a] | Degraded i-PP MFR[b] (g/10 min) | Sulfide MFR[c] (g/10 min) | Cured Gel Content (wt %) | Bound Polymer (wt %) |
|---|---|---|---|---|
| TATM | 42 | 46 | 47 | 61 |
| TAP | 47 | 54 | 37 | 55 |
| PETAE | 52 | 55 | 54 | 41 |
| PETA | 54 | 62 | 30 | 42 |

[a]TAP = triallyl phosphate; PETAE = pentaerythritol triallyl ether; PETA = pentaerythritol triacrylate.
[b]Degradation conditions: [Coagent] = 1.0 wt %; [DCP] = 0.1 wt %; T = 180° C.; 7 min.
[c]Thiol-ene conditions: [MPTMS] = 3.9 wt %; [L-101] = 0.1 wt %; T = 170° C.; 15 min.

TABLE 6

MPTMS addition to HDPE[a]

| MPTMS (mmole/g) | Starting MFI[b] (g/10 min) | Final MFI[b] (g/10 min) | Gel Content (wt %) |
|---|---|---|---|
| 0.1 | 12.3 | 11.9 | 35 |
| 0.2 | 12.3 | 12.8 | 56 |
| 0.3 | 12.3 | 12.6 | 62 |

[a][DCP] = 0.5 wt %; T = 170° C.; 15 min.
[b]MFI measured at 190° C. using 5 kg load.

TABLE 7

BAS addition to PIB[a]

| Polymer | Grafted BAS Content (µmole/g) | G'[b] (kPa) | G''[b] (kPa) | tanδ[b] |
|---|---|---|---|---|
| Unmodified PIB | — | 173 | 34 | 0.20 |
| PIB-g-BAS | 5.4 | 115 | 58 | 0.50 |
| Degraded PIB | — | 40 | 42 | 1.04 |

[a][DCP] = 0.5 wt %; T = 160° C.; 25 min.
[b]Measured at 40° C. using 3° arc at 1 Hz.

While this invention has been described with reference to illustrative embodiments and examples, the description is not intended to be construed in a limiting sense. Thus, various modifications of the illustrative embodiments, as well as other embodiments of the invention, will be apparent to persons skilled in the art upon reference to this description. It is therefore contemplated that the appended claims will cover any such modifications or embodiments.

All publications, patents and patent applications referred to herein are incorporated by reference in their entirety to the same extent as if each individual publication, patent or patent application was specifically and individually indicated to be incorporated by reference in its entirety.

What is claimed is:

1. A process for preparing a functionalised polyolefin, comprising reacting: (i) a polyolefin, (ii) a compound containing a functional group, and (iii) a coagent compound having Formula I:

$$X_n\text{—}Y\text{—}Z_m \quad (I)$$

wherein:
Y is a core moiety;
Z is a moiety containing a carbon-carbon double bond or a carbon-carbon triple bond;
X is a moiety different than Z and the bond between X and Y may be a single bond or a double bond;
n is a whole number greater than or equal to 0, with the provisos that: (i) when n is 0, Y is an organic moiety, and (ii) when n is a whole number greater than 0, Y is an inorganic moiety;
m is a whole number greater than 2; and
m+n equals a number up to the valence of Y;
the coagent compound being selected from the group consisting of a polyallyl compound, a polyvinyl compound and mixtures thereof;
wherein: (a) the coagent compound is initially reacted with one of the compound containing a functional group and the polyolefin to form a product that is then reacted with the other of the compound containing a functional group and the polyolefin; and
(b) the compound containing a functional group is substantially inert in free radical-mediated polymerization reactions and in free radical-mediated grafting reactions.

2. The process defined in claim 1, wherein Y is an inorganic moiety (e.g., silicon or phosphorus).

3. The process defined in claim 1, wherein Y is an organic moiety.

4. The process defined in claim 3, wherein the organic moiety comprises a $C_1$-$C_{10}$ alkyl moiety.

5. The process defined in claim 3, wherein the organic moiety comprises a $C_5$-$C_{20}$ aryl moiety, optionally substituted with one or more $C_1$-$C_{10}$ alkyl moieties.

6. The process defined in claim 1, wherein Z comprises a vinyl moiety.

7. The process defined in claim 1, wherein Z comprises an allyl moiety.

8. The process defined in claim 1, wherein X comprises an $sp^2$-hybridized moiety.

9. The process defined in claim 8, wherein the $sp^2$-hybridized moiety comprises oxygen.

10. The process defined in claim 1, wherein X comprises a $C_1$-$C_{15}$ is aliphatic moiety.

11. The process defined in claim 10, wherein the aliphatic moiety contains one or more heteroatoms.

12. The process defined in claim 1, wherein the polyallyl compound is selected from the group comprising triallyl trimellitate (TATM), triallyl phosphate (TAP), pentaerythritol diallyl ether (PE(Di)AE), pentaerythritol triallyl ether (PE(Tri)AE), pentaerythritol tetraallyl ether (PE(Tetra)AE), 1,3,5-triallylmesate, triallyl cyanurate and mixtures thereof.

13. The process defined in claim 1, wherein the polyallyl compound is selected from the group comprising triallyl trimellitate (TATM), 1,3,5-triallylmesate and mixtures thereof.

14. The process defined in claim 1, where the polyvinyl compound is selected from the group comprising natural oil, divinylbenzene and mixtures thereof.

15. The process defined in claim 1, wherein the compound containing a functional group and the coagent compound are initially reacted to form an adduct and the adduct is reacted with the polyolefin.

16. The process defined in claim 1, wherein the polyolefin is initially reacted with the coagent compound to form a product and thereafter the product is reacted with the compound containing a functional group.

17. The process defined in claim 1, wherein the polyolefin comprises a homopolymer, a copolymer or a terpolymer derived from the polymerization of at least one olefin monomer.

18. The process defined in claim 17, wherein the at least one olefin monomer is selected from the group comprising α-olefin monomers, diolefin monomers and polymerizable monomers containing at least one internal olefin linkage.

19. The process defined in claim 17, wherein the olefin monomer comprises an α-olefin monomer.

20. The process defined in claim 19, wherein the α-olefin monomer is selected from the group comprising propylene, 1-butene, isobutene, 1-pentene, 1-hexene, 1-octene, branched isomers thereof, styrene, α-methylstyrene and mixtures thereof.

21. The process defined in claim 19, wherein the α-olefin monomer comprises propylene.

22. The process defined in claim 17, wherein the olefin monomer comprises a diolefin monomer.

23. The process defined in claim 22, wherein the diolefin monomer is selected from the group comprising 1,3-butadiene, isoprene, 2,3-dimethyl-1,3-butadiene, 2-ethyl-1,3-butadiene, piperylene, myrcene, allene, 1,2-butadiene, 1,4,9-decatrienes, 1,4-hexadiene, 1,6-octadiene, 1,5-hexadiene, 4-methyl-1,4-hexadiene, 5-methyl-1,4-hexadiene, 7-methyl-1,6-octadiene, phenylbutadiene, pentadiene and mixtures thereof.

24. The process defined in claim 22, wherein the diolefin monomer comprises a bicyclic compound.

25. The process defined in claim 22, wherein the diolefin monomer is selected from the group comprising 1,4-cyclohexadiene, 1,5-cyclooctadiene, 1,5-cyclododecadiene, methyltetrahydroindene, dicyclopentadiene, bicyclo hepta-2,5-2,5-diene and mixtures thereof.

26. The process defined in claim 1, wherein the polyolefin is a copolymer derived from polymerization of a mixture of ethylene and at least one α-olefin.

27. The process defined in claim 1, wherein the polyolefin is a copolymer derived from polymerization of a mixture of ethylene and propylene.

28. The process defined in claim 1, wherein the polyolefin is a copolymer derived from polymerization of a mixture of ethylene, at least one α-olefin and at least one diolefin monomer.

29. The process defined in claim 1, wherein the polyolefin is a copolymer derived from polymerization of a mixture of ethylene, propylene and one or both of 5-ethylidene-2-norbornene and 1,5-hexadiene.

30. The process defined in claim 28, wherein the mixture comprises from about 0.5 to about 15 weight percent of the diolefin monomer.

31. The process defined in claim 1, wherein the polyolefin is selected from the group comprising polypropylene, ethylene-propylene copolymers, polyisobutylene and mixtures thereof.

32. The process defined in claim 1, wherein the polyolefin comprises polypropylene.

33. The process defined in claim 1, wherein the polyolefin has a molecular weight (Mn) in the range of from about 10,000 to about 100,000.

34. The process defined in claim 1, wherein the polyolefin has a molecular weight (Mn) in the range of from about 20,000 to about 80,000.

35. The process defined in claim 1, wherein the compound containing a functional group is selected from the group comprising thiols, epoxides, anhydrides, carboxylic acids, amines, amides, boron-containing compounds, silicon-containing compounds, cyano-containing compounds, sulfates, sulfonates, sulfites, esters, thioesters, dithioesters, ether, halides, phosphates, phosphonates, phosphines, phosphites, olefins, other compounds containing polar moieties and mixtures thereof.

36. The process defined in claim 1, wherein the compound containing a functional group is selected from the group comprising thiols, silanes, epoxides, anhydrides and mixtures thereof.

37. The process defined in claim 1, wherein the compound containing a functional group is selected from the group comprising (3-mercaptopropyl)-trimethoxysilane, mercaptoundecanoic acid, mercaptosuccinic anhydride, mercaptoethanolamine, mercaptoepoxide and mixtures thereof.

38. The process defined in claim 15, wherein the adduct is selected from the group comprising a bisallylsulfide, a bisallylepoxide and mixtures thereof.

39. The process defined in claim 38, wherein the bisallylsulfide has the following formula a structural isomer thereof or a mixture of structural isomers thereof.

40. The process defined in claim 38, wherein the bisallylepoxide has the following formula a structural isomer thereof or a mixture of structural isomers thereof.

41. The process defined in claim 1, wherein the process is carried out in the absence of solvent.

42. The process defined in claim 1, wherein the process is carried out in the presence of a solvent.

43. The process defined in claim 42, wherein the reactants are soluble in the solvent.

44. The process defined in claim 1, wherein at least one step of the process is conducted at a temperature above the melting point of the polyolefin.

45. A functionalised polyolefin prepared by the process defined in claim 1.

46. The process defined in claim 1, comprising the further step of contacting the functionalised polyolefin with a siliceous particulate material.

47. The product produced by the process defined in claim 46.

48. A process for preparing a functionalised polyolefin, comprising reacting: (i) a polyolefin, (ii) a compound containing a functional group selected from the group consisting of (3-mercaptopropyl)-trimethoxysilane, mercaptoundecanoic acid, mercaptosuccinic anhydride, mercaptoethanolamine, mercaptoepoxide and mixtures thereof, and (iii) a coagent compound having Formula I:

$$X_n\text{—}Y\text{—}Z_m \quad (I)$$

wherein:
Y is a core moiety;
Z is a moiety containing a carbon-carbon double bond or a carbon-carbon triple bond;
X is a moiety different than Z and the bond between X and Y may be a single bond or a double bond;
n is a whole number greater than or equal to 0, with the provisos that: (i) when n is 0, Y is an organic moiety, and (ii) when n is a whole number greater than 0, Y is an inorganic moiety;
m is a whole number greater than 2; and
m+n equals a number up to the valence of Y;
wherein: (a) the coagent compound is initially reacted with one of the compound containing a functional group and the polyolefin to form a product that is then reacted with the other of the compound containing a functional group and the polyolefin; and
(b) the compound containing a functional group is substantially inert in free radical-mediated polymerization reactions and in free radical-mediated grafting reactions.

49. A process for preparing a functionalised polyolefin, comprising:
(1) reacting a compound containing a functional group and a coagent compound to produce an adduct selected from the group consisting of a bisallylsulfide, a bisallylepoxide and mixtures thereof, the compound containing a functional group being substantially inert in free radical-mediated polymerization reactions and in free radical-mediated grafting reactions, and the coagent compound having Formula I:

$$X_n\text{—}Y\text{—}Z_m \quad (I)$$

wherein:
Y is a core moiety;
Z is a moiety containing a carbon-carbon double bond or a carbon-carbon triple bond;
X is a moiety different than Z and the bond between X and Y may be a single bond or a double bond;
n is a whole number greater than or equal to 0, with the provisos that: (i) when n is 0, Y is an organic moiety, and (ii) when n is a whole number greater than 0, Y is an inorganic moiety;
m is a whole number greater than 2; and
m +n equals a number up to the valence of Y; and
(2) reacting the adduct with a polyolefin.

50. The process defined in claim 49, wherein the bisallylsulfide has the following formula a structural isomer thereof or a mixture of structural isomers thereof.

* * * * *

UNITED STATES PATENT AND TRADEMARK OFFICE
CERTIFICATE OF CORRECTION

| | | |
|---|---|---|
| PATENT NO. | : 7,858,705 B2 | Page 1 of 1 |
| APPLICATION NO. | : 11/266487 | |
| DATED | : December 28, 2010 | |
| INVENTOR(S) | : John Scott Parent and Saurav Sankar Sengupta | |

It is certified that error appears in the above-identified patent and that said Letters Patent is hereby corrected as shown below:

In the title, item (54) and col. 1, line 3, "Manufacturer" should be --Manufacture--.

Col. 20, lines 35-36, in claim 25, "bicyclo hepta-2.5-2,5-diene" should be --bicyclo [2.2.1] hepta-2,5-2,5-diene--.

Col. 20, line 53, in claim 30, "diolefm" should be --diolefin--.

Signed and Sealed this
Twenty-second Day of March, 2011

David J. Kappos
*Director of the United States Patent and Trademark Office*